United States Patent [19]

Manning et al.

[11] Patent Number: 4,551,445
[45] Date of Patent: * Nov. 5, 1985

[54] DERIVATIVES OF ARGININE VASOPRESSIN ANTAGONISTS

[75] Inventors: Maurice Manning, Toledo, Ohio; Wilbur H. Sawyer, Scarsdale, N.Y.

[73] Assignees: The Medical College of Ohio, Toledo, Ohio; The Trustees of Columbia University, New York, N.Y.

[*] Notice: The portion of the term of this patent subsequent to Aug. 16, 2000 has been disclaimed.

[21] Appl. No.: 541,979

[22] Filed: Oct. 14, 1983

[51] Int. Cl.[4] .................... A61K 37/00; C07C 103/52
[52] U.S. Cl. ............................................ 514/9; 514/7; 514/15; 514/16; 514/17; 260/112.5 R
[58] Field of Search ................................ 260/112.5 R

[56] References Cited

U.S. PATENT DOCUMENTS

| | | | |
|---|---|---|---|
| 3,371,080 | 2/1968 | Boissonnas et al. | 260/112.5 R |
| 3,415,805 | 12/1968 | Siedel et al. | 260/112.5 R |
| 3,418,307 | 12/1968 | Boissonnas et al. | 260/112.5 R |
| 3,454,549 | 7/1969 | Boissonnas et al. | 260/112.5 R |
| 3,497,491 | 2/1970 | Zaoral et al. | 260/112.5 R |
| 3,691,147 | 9/1972 | Manning | 260/112.5 R |
| 3,700,652 | 10/1972 | Manning | 260/112.5 R |
| 3,752,799 | 8/1973 | Jost | 260/112.5 R |
| 3,816,385 | 6/1974 | Gillessen et al. | 260/112.5 R |
| 3,883,498 | 5/1975 | Gillessen et al. | 260/112.5 R |
| 3,980,631 | 9/1976 | Prochazka et al. | 260/112.5 R |
| 4,081,533 | 3/1978 | Cheesman | 424/177 |
| 4,148,787 | 4/1979 | Mulder | 260/112.5 R |
| 4,237,119 | 12/1980 | Cort et al. | 424/177 |
| 4,285,858 | 8/1981 | Cort et al. | 260/112.5 R |
| 4,367,225 | 1/1983 | Manning et al. | 424/177 |
| 4,399,125 | 8/1983 | Manning et al. | 260/112.5 R |

OTHER PUBLICATIONS

Dyckes et al., 17 *J. Med. Chem.* 250 (1974).
Manning et al., 20 *J. Med. Chem.* 1228 (1977).
Bankowski et al., 21 *J. Med. Chem.* 850 (1978).
Kruszynski et al., 23 *J. Med. Chem.* 364 (1980).
Lowbridge et al., 21 *J. Med. Chem.* 313 (1978).
Chan et al., 161 *Science* 280 (1968).
Chan et al., 174 *J. Pharmacol. Exp. Ther.* 541 (1970).
Chan et al., 196 *J. Pharmacol. Exp. Ther.* 746 (1976).
Nestor et al., 18 *J. Med. Chem.* 1022 (1975).
Larsson et al., 21 *J. Med. Chem.* 352 (1978).
Sawyer et al., 212 *Science* 49 (1981).
Manning et al., 24 *J. Med. Chem.* 701 (1981).
Merrifield, 85 *J. Am. Chem. Soc.* 2149 (1963).
Merrifield, 3 *Biochemistry* 1385 (1964).
Manning, 90 *J. Am. Chem. Soc.* 1348 (1968).
Manning et al., 19 *J. Med. Chem.* 376 (1976).
Lowbridge et al., 20 *J. Med. Chem.* 1173 (1977).
Manning et al., 16 *J. Med. Chem.* 975 (1973).

Felix et al., 10 *J. Peptide Protein Res.* 299 (1977).
Botos et al., 22 *J. Med. Chem.* 926 (1979).
Hope et al., 237 *J. Biol. Chem.* 1563 (1962).
Schultz et al., 9 *J. Med. Chem.* 647 (1966).
Nestor et al., 18 *J. Med. Chem.* 284 (1975).
Huguenin et al., 39 *Helv. Chem. Acta*, 695 (1966).
Manning et al., 19 *J. Med. Chem.* 842 (1976).
Law et al., 82 *J. Am. Chem. Soc.* 4579 (1960).
Manning et al., Peptides, Structure, Function, Dan H. Rich and E. Gross, eds., Pierce Chemical Co., 257 (1981).
Manning et al., 25 *J. Med. Chem.* 45 (1982).
Butlen et al., 14 *Mol. Pharmacol.* 1006 (1978).
Sawyer et al., 5 *Endocrinology* 140 (1974).
D. B. Case et al., 21 *Progress in Cardiovascular Diseases* 195 (1978).
Bartter et al., 42 *Am. J. Med.* 790 (1967).
Gisin, 56 *Helv. Chem. Acta.* 1476 (1973).
Spackman et al., 30 *Anal. Chem.* 1190 (1958).
Konig et al., 103 *Chem. Ber.* 788 (1970).
Manning, 90 *J. Am. Chem. Soc.* 1348 (1968).
du Vigneaud, 76 *J. Am. Chem. Soc.* 3115 (1954).
Hope et al., 237 *J. Biol. Chem.* 1563 (1962).
Manning et al., 38 *J. Chromatog.* 396 (1968).
Moore, 238 *J. Biol. Chem.* 235 (1963).
Bodanszky et al., 81 *J. Am. Chem. Soc.* 5688 (1959).
Bodanszky et al., 39 *J. Org. Chem.* 444 (1974).
Dyckes et al., 17 *J. Med. Chem.* 969 (1974).
Schild et al., 2 *Br. J. Pharmacol.* 189 (1947).
Sawyer et al., 63 *Endocrinology* 694 (1958).
Manning et al., 227 *Nature* No. 5259, 715 (1970).
Baxter et al., 8 *Biochemistry* 3592 (1962).
Manning et al., 9 *Biochemistry* 3925 (1970).
Manning et al., 21 *J. Med. Chem.* 179 (1978).

*Primary Examiner*—Delbert R. Phillips
*Attorney, Agent, or Firm*—Emch, Schaffer, Schaub & Porcello Co.

[57] ABSTRACT

Compounds acting as antagonists of the antidiuretic activity of arginine vasopressin are those of the formula

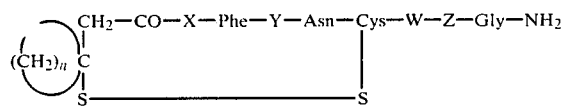

wherein n is 4 or 5; X is D—Tyr(R), D—Phe, D—Val, D—Leu, D—Ile, D—Nva, D—Nle, D—Cha, D—Abu, D—Thr, D—Met, D—Asn, or D—Gin; Y is Ile, Thr, Gln, Ala, Lys, Cha, Nva, Nle, Orn, Ser, Asn, Met, Abu or Leu; W is (D— or L—)Pro, Hy—Pro or $\Delta^3$—Pro; Z is (D— or L—)Arg, Orn or Lys and R is methyl, ethyl, propyl or butyl.

26 Claims, No Drawings

DERIVATIVES OF ARGININE VASOPRESSIN ANTAGONISTS

The invention described herein was made in the course of work under a grant or award from the Department of Health and Human Services.

DESCRIPTION

1. Background of the Invention

This invention relates to novel peptides which antagonize the antidiuretic and/or vasopressor action of arginine vasopressin in vivo.

2. Prior Art Statement

Attempts to develop clincally useful synthetic antagonists of in vivo antidiuretic and/or vasopressor responses to arginine vasopressin, the anti-diuretic hormone (ADH), have led to the synthesis and pharmacological evaluation of hundreds of analogs of the neurohypophysial peptides, oxytocin and vasopressin.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1970) at 541 and vol. 196 (1976) at 746; Nestor et al., *J. Med. Chem.*, vol. 18 (1975) at 1022 and Larsson et al., *J. Med. Chem.*, vol. 21 (1978) at 352, herein incorporated by reference. None of the compounds reported has been pharmacologically or clinically useful as an antidiuretic antagonist.

The synthesis and evaluation of vasopressin analogs, incorporating etherified tyrosine at the 2-position, valine at the 4-position and D- or L-arginine at the 8-position, which antagonize the anti-antidiuretic action of ADH in vivo, have been reported by Sawyer et al., *Science*, vol. 212 (1981) at 49; Manning et al., *J. Med. Chem.*, vol. 24 (1981) at 701; and Manning et al., U.S. Pat. Nos. 4,367,225 and 4,399,125, herein incorporated by reference.

Design of tissue-specific agonists and antagonists in the field of neurohypophysial peptides has been considered by Sawyer et al., *Molecular and Cellular Endocrinology*, vol. 22 (1981), 117–134; Manning et al., "The Pituitary, Beardwell et al., eds., Butterworths, Kent, England (1981), 265–296; Manning et al., "Peptides, Synthesis, Structure, Function," Rich et al., eds., Pierce Chemical Co., (1981) at 257 and Manning et al., *J. Med. Chem.*, vol. 25 (1982) at 414.

It is therefore apparent that the correlation between structure of neurohyophysial peptides and behavior in vivo is not well understood and there is a continuing need for the development of pharmacologically and clinically effective antagonists of the antidiuretic action of arginine vasopressin.

OBJECT OF THE INVENTION

It is the object of the invention to provide novel antagonists of the antidiurectic action of ADH, which are effective in vivo.

SUMMARY OF THE INVENTION

This invention relates to novel antagonists of the antidiuretic action of ADH, which are compounds of the formula

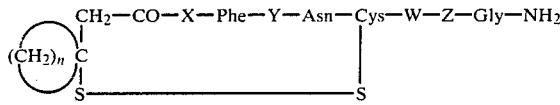

wherein n is 4 or 5; X is D—Tyr(R), D—Phe, D—Val, D—Leu, D—Ile, D—Nva, D—Nle, D—Cha, D—Abu, D—Thr, D—Met, D—Asn or D—Gln; Y is Ile, Thr, Gln, Ala, Lys, Cha, Nva, Nle, Orn, Ser. Asn, Met, Abu, or Leu; W is (D— or L—)Pro, Hy—Pro or $\Delta^3$—Pro; Z is (D— or L—)Arg, Orn or Lys and R is methyl, ethyl propyl or butyl.

This invention further relates to a method for antagonizing the in vivo response to ADH, comprising administering to an animal being treated an amount of one of the foregoing compounds, in admixture with a physiologically and pharmaceutically acceptable carrier, effective to antagonize the antidiuretic response to ADH.

DETAILED DESCRIPTION

Compounds of the invention are derivatives of arginine vasopressin. Amino acids are in the L-form, unless otherwise indicated. The correlation between full names and abbreviations is:

AVP, arginine vasopressin;

$d(CH_2)_5AVP$, [1-($\beta$-mercapto-$\beta$,$\beta$-cyclopentamethylenepropionic acid)]arginine vasopressin;

$d(CH_2)_5VDAVP$, [1-($\beta$-mercapto-$\beta$,$\beta$-cyclopentamethylenepropionic acid), 4-valine, 8-D-arginine]-vasopressin;

$d(CH_2)_5Tyr(Me)VDAVP$, [1-($\beta$-mercapto-$\beta$,$\beta$-cyclopentamethylenepropionic acid), 2-O-methyltyrosine, 4-valine, 8-D-arginine]vasopressin;

$d(CH_2)_5$-D-TyrVDAVP, [1-($\beta$-mercapto-$\beta$,$\beta$-cyclopentamethylenepropionic acid), 2-D-tyrosine, 4-valine, 8-D-arginine]vasopressin;

$d(CH_2)_5$-D-TyrVAVP, [1-($\beta$-mercapto-$\beta$,$\beta$-cyclopentamethylenepropionic acid), 2-D-tyrosine, 4-valine]-arginine vasopressin;

$d(CH_2)_5Tyr(Me)AVP$, [1-($\beta$-mercapto-$\beta$,$\beta$-cyclopentamethylenepropionic acid), 2-O-methyltyrosine]-arginine vasopressin;

$d(CH_2)_5$-D-Tyr(Me)$^2$AVP, [1-($\beta$-mercapto-$\beta$,$\beta$-cyclopentamethylenepropionic acid), 2-D-(O-methyl)tyrosine]-arginine vasopressin;

$d(CH_2)_5$D-Phe$^2$Ile$^4$AVP, [1-($\beta$-mercapto-$\beta$,$\beta$-cyclopentamethylenepropionic acid), 2-D-phenylalanine, 4-isoleucine]-arginine vasopressin;

$d(CH_2)_5$D-Phe$^2$Thr$^4$AVP, [1-($\beta$-mercapto-$\beta$,$\beta$-cyclopentamethylenepropionic acid), 2-D-phenylalanine, 4-threonine]-arginine vasopressin;

$d(CH_2)_5$D-Phe$^2$AVP, [1-($\beta$-mercapto-$\beta$,$\beta$-cyclopentamethylenepropionic acid), 2-D-phenylalanine]-arginine vasopressin;

$d(CH_2)_5$D-Phe$^2$Ala$^4$AVP, [1-($\beta$-mercapto-$\beta$,$\beta$-cyclopentamethylenepropionic acid), 2-D-phenylalanine, 4-alanine]-arginine vasopressin;

$d(CH_2)_5$D-Phe$^2$Lys$^4$AVP, [1-($\beta$-mercapto-$\beta$,$\beta$-cyclopentamethylenepropionic acid), 2-D-phenylalanine, 4-lysine]-arginine vasopressin;

$d(CH_2)_5$D-Phe$^2$Cha$^4$AVP, [1-($\beta$-mercapto-$\beta$,$\beta$-cyclopentamethylenepropionic acid), 2-D-phenylalanine, 4-cyclohexylalanine]-arginine vasopressin;

$d(CH_2)_5$D-Phe$^2$nVa$^4$AVP, [1-($\beta$-mercapto-$\beta$,$\beta$-cyclopentamethylenepropionic acid), 2-D-phenylalanine, 4-norvaline]-arginine vasopressin;

d(CH$_2$)$_5$D-Phe$^2$Leu$^4$AVP, [1-($\beta$-mercapto-$\beta$,$\beta$-cyclopentamethylenepropionic acid), 2-D-phenylalanine, 4-leucine]-arginine vasopressin;

d(CH$_2$)$_5$D-Phe$^2$Phe$^4$AVP, [1-($\beta$-mercapto-$\beta$,$\beta$-cyclopentamethylenepropionic acid), 2-D-phenylalanine, 4-phenylalanine]-arginine vasopressin;

d(CH$_2$)$_5$D-Phe$^2$Tyr$^4$AVP, [1-($\beta$-mercapto-$\beta$,$\beta$-cyclopentamethylenepropionic acid), 2-D-phenylalanine, 4-tyrosine]-arginine vasopressin;

d(CH$_2$)$_5$D-Phe$^2$Gly$^4$AVP, [1-($\beta$-mercapto-$\beta$,$\beta$-cyclopentamethylenepropionic acid), 2-D-phenylalanine, 4-glycine]-arginine vasopressin;

d(CH$_2$)$_5$D-Phe$^2$Abu$^4$AVP, [1-($\beta$-mercapto-$\beta$,$\beta$-cyclopentamethylenepropionic acid), 2-D-phenylalanine, 4-aminobutyric acid]-arginine vasopressin;

d(CH$_2$)$_5$D-Ile$^2$VAVP, [1-($\beta$-mercapto-$\beta$,$\beta$-cyclopentamethylenepropionic acid), 2-D-isoleucine, 4-valine]-arginine vasopressin;

d(CH$_2$)$_5$D-Ile$^2$Abu$^4$AVP, [1-($\beta$-mercapto-$\beta$,$\beta$-cyclopentamethylenepropionic acid), 2-D-isoleucine, 4-$\alpha$-aminobutyric acid]-arginine vasopressin;

d(CH$_2$)$_5$D-Ile$^2$Ile$^4$AVP, [1-($\beta$-mercapto-$\beta$,$\beta$-cyclopentamethylenepropionic acid), 2-D-isoleucine, 4-isoleucine]-arginine vasopressin;

d(CH$_2$)$_5$D-Ile$^2$Thr$^4$AVP, [1-($\beta$-mercapto-$\beta$,$\beta$-cyclopentamethylenepropionic acid), 2-D-isoleucine, 4-threonine]-arginine vasopressin;

d(CH$_2$)$_5$D-Ile$^2$AVP, [1-($\beta$-mercapto-$\beta$,$\beta$-cyclopentamethylenepropionic acid), 2-D-isoleucine]-arginine vasopressin;

d(CH$_2$)$_5$D-Ile$^2$Ala$^4$AVP, [1-($\beta$-mercapto-$\beta$,$\beta$-cyclopentamethylenepropionic acid), 2-D-isoleucine, 4-alanine]-arginine vasopressin;

d(CH$_2$)$_5$D-Ile$^2$Lys$^4$AVP, [1-($\beta$-mercapto-$\beta$,$\beta$-cyclopentamethylenepropionic acid), 2-D-isoleucine, 4-lysine]-arginine vaospressin;

d(CH$_2$)$_5$D-Ile$^2$Nva$^4$AVP, [1-($\beta$-mercapto-$\beta$,$\beta$-cyclopentamethylenepropionic acid), 2-D-isoleucine, 4-norvaline]-arginine vasopressin;

d(CH$_2$)$_5$D-Ile$^2$Cha$^4$AVP, [1-($\beta$-mercapto-$\beta$,$\beta$-cyclopentamethylenepropionic acid), 2-D-isoleucine, 4-cyclohexylalanine]-arginine vasopressin;

d(CH$_2$)$_5$D-Ile$^2$Leu$^4$AVP, [1-($\beta$-mercapto-$\beta$,$\beta$-cyclopentamethylenepropionic acid), 2-D-isoleucine, 4-leucine]-arginine vasopressin;

d(CH$_2$)$_5$D-Ile$^2$Phe$^4$AVP, [1-($\beta$-mercapto-$\beta$,$\beta$-cyclopentamethylenepropionic acid), 2-D-isoleucine, 4-phenylalanine]-arginine vasopressin;

d(CH$_2$)$_5$D-Ile$^2$Tyr$^4$AVP, [1-($\beta$-mercapto-$\beta$,$\beta$-cyclopentamethylenepropionic acid), 2-D-isoleucine, 4-tyrosine]-arginine vasopressin;

d(CH$_2$)$_5$D-Ile$^2$Gly$^4$AVP, [1-($\beta$-mercapto-$\beta$,$\beta$-cyclopentamethylenepropionic acid), 2-D-isoleucine, 4-glycine]-arginine vasopressin;

d(CH$_2$)$_5$D-Ile$^2$Asn$^4$AVP, [1-($\beta$-mercapto-$\beta$,$\beta$-cyclopentamethylenepropionic acid), 2-D-isoleucine, 4-asparagine]-arginine vasopressin;

d(CH$_2$)$_5$D-Ile$^2$Met$^4$AVP, [1-($\beta$-mercapto-$\beta$,$\beta$-cyclopentamethylenepropionic acid), 2-D-isoleucine, 4-methionine]-arginine vasopressin;

d(CH$_2$)$_5$D-Ile$^2$Nle$^4$AVP, [1-($\beta$-mercapto-$\beta$,$\beta$-cyclopentamethylenepropionic acid), 2-O-isoleucine, 4-norleucine]-arginine vasopressin;

d(CH$_2$)$_5$D-Ile$^2$AVP, [1-($\beta$-mercapto-$\beta$,$\beta$-cyclopentamethylenepropionic acid), 2-D-isoleucine]-arginine vasopressin;

d(CH$_2$)$_5$D-Phe$^2$Abu$^4$AVP, [1-($\beta$-mercapto-$\beta$,$\beta$-cyclopentamethylenepropionic acid), 2-D-phenylalanine, 4-$\alpha$-aminoisobutyric acid]-arginine vasopressin;

d(CH$_2$)$_5$D-Phe$^2$Nle$^4$AVP, [1-($\beta$-mercapto-$\beta$,$\beta$-cyclopentamethylenepropionic acid), 2-D-phenylalanine, 4-norleucine]-arginine vasopressin;

d(CH$_2$)$_5$D-Ile$^2$Leu$^4$AVP, [1-($\beta$-mercapto-$\beta$,$\beta$-cyclopentamethylenepropionic acid), 2-D-isoleucine, 4-leucine]-arginine vasopressin and d(CH$_2$)$_5$D-Phe$^2$Ile$^4$Hy-Pro$^7$AVP, [1-($\beta$-mercapto-$\beta$,$\beta$-cyclopentamethylenepropionic acid), 2-D-phenylalanine, 4-leucine, 7-hydroxyproline]-arginine vasopressin.

The active peptides were synthesized by solid phase synthesis, as described by Bankowski et al. (1978), infra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975; Kruszynski et al. (1980), infra; Sawywer et al., (1981), supra or Manning et al. (1981), supra.

The discovery of the antidiuretic antagonists d(CH$_2$)$_5$Tyr(alk)VAVP, Sawyer et al. (1981), supra, and Manning et al. (1981), supra, led to the synthesis of various analogs having a cyclopentamethylene ring structure and various substituents at the 2-position.

Based on the studies cited above, it was assumed that a valine substituent at the 4-position was critical for antidiuretic antagonism. Thus, d(CH$_2$)$_n$Tyr(alk)AVP, wherein alk is methyl or ethyl, which have glutamine at the 4-position, are potent vasopressor antagonists but weak antidiuretic antagonists:

| Analog | Agonistic Activities units/mg Antidiuretic | Antagonistic Activities units/mg Antivasopressor | |
|---|---|---|---|
| | | ED nmoles/kg | pA$_2$ |
| d(CH$_2$)Tyr(Me)AVP | 0.31 ± 0.07 | 0.16 | 8.62 ± 0.03 |
| d(CH$_2$)$_5$Tyr(Et)AVP | 0.079 ± 0.004 | 0.31 | 8.47 ± 0.04 |

As recited in U.S. Pat. Nos. 4,367,225 and 4,399,125, replacement of Gln by Val at the 4-position produced potent antidiuretic antagonists.

It was surprisingly found, in accordance with the present invention, that compounds of the formula d(CH$_2$)$_n$X$^2$Y$^4$AVP, when X is 2-D-phenylalanine and 2-D-isoleucine, can have variety of substituents at the 4-position, including glutamine, without loss of antidiuretic antagonistic activity. Accordingly compounds of Formulas I and II, having various substituents at the 4-position, are active as antagonists of the antidiuretic action of arginine vasopressin.

It was also surprisingly found that a representative compound of Formula III, [1-($\beta$-mercapto-$\beta$,$\beta$-cyclopentamethylenepropionic acid), 2-D-(O-methyl)-tyrosine]-arginine vasopressin, was active as an antagonist of the antidiuretic action of ADH, whereas the 2-L-Tyr(Me) isomer was not, Kruszynski, *J. Med. Chem.*, vol. 23 (1980), 364.

Preferred compounds of the invention are those of Formulas I, II and III:

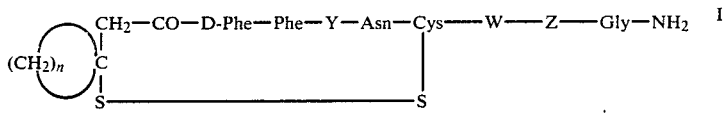

wherein n is 4 or 5; Y is Ile, Thr, Gln, Ala, Lys, Cha, Nva, Orn, Ser, Asn, Abu, Nle or Leu; W is (D— or L—Pro), Hy—Pro or Δ³—Pro; and Z is (D— or L—)Arg, Orn or Lys;

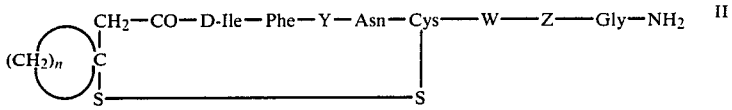

wherein n is 4 or 5; Y is Gln, Ala, Lys, Cha, Nva, Leu, Orn, Asn, Ser, Met, Nle, Abu, Ile or Thr; W is (D— or L—)Pro, Hy—Pro or Δ³—Pro and Z is (D— or L—)Arg, Lys or Orn; or

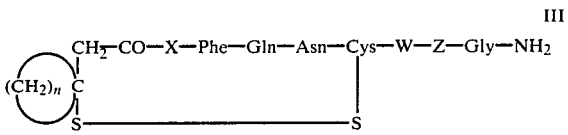

wherein n is 4 or 5; X is D—Tyr(R); R is methyl, ethyl, propyl or butyl; W is (D— or L—)Pro, Hy—Pro or Δ³—Pro and Z is (D— or L—)Arg, Orn or Lys.

It will be understood, that when the compounds of the invention are those wherein X is D—Tyr(R), R includes isomeric propyl and butyl compounds.

Preferred compounds of the invention and of Formulas I, II and III are those wherein n is 5, W is Pro and Z is (D— or L—)Arg.

Most preferred compounds of Formula I are those wherrein Z is Arg or wherein Y is Ile, Thr, Ala or Abu. A compound of Formula I, wherein Z is Arg and Y is Ile is the most potent antidiuretic antagonist found thus far. Unlike many AVP derivatives, this compound has no antidiuretic agonistic activity.

Contemplated equivalents of compounds of Formula I are those wherein Y is Asn, Met or AlloIle.

It will also be understood that, when alkyl substituents (R) can be linear or branched, contemplated equivalents include all possible isomers.

Most preferred compounds of Formula II are those wherein Y is Abu, Ile, Ala or Thr or wherein Z is Arg.

Most preferred compounds of Formula III are those wherein X is D—Tyr(Me) or Z is Arg.

The compounds of this invention are accordingly very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et al., Am. J. Med., vol. 42 (1967) at 790.

The compounds of this invention can be employed in mixtures with conventional excipients, i.e., physiologically and pharmaceutically acceptable organic or inorganic carriers suitable for parenteral or other application, provided that the carriers do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing the osmotic pressure, buffers, coloring, flavoring and/or aromatic substances, which do not deleteriously interact with the active compounds.

For parenteral or intranasal application, solutions, preferably aqueous solutions, as well as suspensions, emulsions or implants, including suppositories, are particularly suitable. Ampoules are convenient unit dosages.

The compounds of this invention are generally administered to animals, including but not limited to mammals, e.g, livestock, household pets, humans, cattle, cats and dogs. A diuretically effective daily dosage of the active compounds can be administered parenterally in a single dosage or as divided dosages throughout the day.

Parenteral or intranasal administration is preferred. The compounds of this invention are particularly valuable in the treatment of humans afflicted with water retention of any etiology. In this regard, they can be adminstered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organisms being treated. Optimal application rates under/in a given set of conditions can be ascertained by those skilled in the art of using conventional dosage determination tests in view of the above guidelines.

DESCRIPTION OF PREFERRED EMBODIMENT

Preferred antidiuretic antagonists of Formula I are those wherein n is 5; Y is Ile, Thr or Abu; W is Pro and Z is Arg. Most preferably, Y is Ile.

Preferred compounds of Formula II are those wherein n is 5; Y' is Abu, Ile, Ala or Thr; W is Pro and Z is Arg.

Most preferred of the compounds of Formula III is that wherein n is 5, X is D—Tyr(Me), W is Pro and Z is Arg.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta.*, vol. 56 (1973) at 1476 with Boc—Gly until 0.47 mmol./g. and ~0.64 mmol/g were incorporated. Amino acid derivatives, including Boc—Tyr(Me) ($R_f(A)$ 0.7, $R_f(B)$ 0.8) were supplied by Bachem or synthesized.

Triethylamine (TEA) and N-methylmorpholine (NMM) were distilled from ninhydrin.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) was done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol (7:3 v/v); E. butan-1-ol-acetic acid-water (4:1:5 v/v, upper phase); F. butan-1-ol-acetic acid-water-pyridine (15:3:3:10 v/v). The applied loadings were 10–50 g. The minimum length of the chromatograms was 10 cm. Chloroplatinate reagent and iodine vapor were used for development of the chromatograms.

Amino acids analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 μl) in evacuated and sealed ampoules for 18 h at 120° C. The analyses were performed using a Beckman Automatic Amino Acid Analyzer, Model 121. Molar ratios were referred to Gly=1.00. Elemental analyses were performed by Galbraith Laboratories, Inc., Knoxville, Tenn. The analytical results from the elements indicated by their respective symbols were within ±0.4% of theoretical values. Optical rotations were measured with a Bellingham Stanley, Ltd., Model A polarimeter, type pl.

EXAMPLE 1

β-(S-Benzylmercapto)-β,β-cyclopentamethylenepropionyl-Tyr(Me)—Phe—Gln—Asn—Cys(Bzl)—Pro—Arg(Tos)—Gly—NH$_2$ A. Combination of Solid Phase and Solution Methods Boc—Tyr(Me)—Phe—Gln—Asn—Cys(Bzl)—Pro—Arg(Tos)—Gly—NH$_2$, prepared by the method of Bankowski et al., *J. Med. Chem.*, vol. 21 (1978) at 850 (319 mg, 0.26 mmol), was dissolved in CF$_3$COOH (6.5 ml) and stirred at room temperature for 40 mins. Cold ether (20 ml) was added to produce a precipitate, which was filtered and washed with ether (5×10 ml). The product was dried in vacuo over sodium hydroxide pellets. This material (318.5 mg) was dissolved in DMF (0.8 ml), to which was added N-methylmorpholine (10 μl). The resulting solution had a pH of 7–8, measured with moist pH paper. After this neutralized solution was stirred at room temperature for 30 mins, a solution of p-nitrophenyl β-(S-benzylmercapto)-β,β-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp 209°–211° C., $[\alpha]_D^{24} = -43.6°$ (c 0.5, DMF); $R_f(E)$ 0.45, $R_f(F)$ 0.63 Anal. (C$_{73}$H$_{94}$O$_{14}$N$_{14}$S$_3$) C, H, N.

(b) Total Synthesis on Resin

Boc—Tyr(Me)—Phe—Gln—Asn—Cys(Bzl)—Pro—Arg(Tos)—Gly-resin (1.11 g, 0.4 mmol prepared from Boc—Gly-resin using solid phase methodology) was converted to the acyloctapeptide resin (1.167 g, weight gain 57 mg, 97.6% of theory) in one cycle of deprotection, neutralization and coupling with p-nitrophenyl β-(S-benzylmercapto)-β,β-cyclopentamethylenepropionate, see Nestor, supra. The resin was ammonolyzed, Manning, *J. Am. Chem. Soc.*, vol. 90 (1968) at 1348. The product was extracted with DMF. After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp 206°–208° C. (decomp); $R_f(E)$ 0.45; $R_f(F)$ 0.63; $[\alpha]_D^{24} = -43.1°$ (c 1, DMF). Anal. (C$_{73}$H$_{94}$N$_{14}$O$_{14}$S$_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; NH$_3$, 2.95.

EXAMPLE 2

β-(S-Benzylmercapto)-β,β-cyclopentamethylenepropionyl-Tyr(Bzl)—Phe—Gln—Asn—Cys(Bzl)—Pro—Arg(Tos)—Gly—NH$_2$ Boc—Tyr(Bzl)—Phe—Gln—Asn—Cys(Bzl)—Pro—Agr(Tos)—Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl β-(S-benzylmercapto)-β,β-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. Yield: 488 mg (62.4% based on initial Gly content on the resin); mp. 183°–185° C.; $R_f(E)$ 0.38; $R_f(D)$ 0.41; $[\alpha]_D^{23} = -23.9°$ (c 1, DMF). Anal. (C$_{79}$H$_{98}$N$_{14}$O$_{14}$S$_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; NH$_3$.

EXAMPLE 3

[1-(β-Mercapto-β,β-cyclopentamethylenepropionic acid), 2-(O-methyl)tyrosine]-arginine vasopressin.

(a) From Nonapeptide Amide

A solution of the protected nonapeptide amide, prepared as in Example 1, (170 mg, 0.114 mmol) in 400 ml of ammonia (dried over sodium and redistilled) was stirred at the boiling point with sodium from a stick of the metal, contained in a small bore glass tube until a light blue color persisted in the solution for 30 sec, in accordance with duVigneaud, *J. Am. Chem. Soc.*, vol. 76 (1954) at 3115. Dry glacial acetic acid (0.4 ml) was added to discharge the color. The solution was evaporated. A solution of the residue in aqueous acetic acid (0.2%, 800 ml), was treated with 2M ammonium hydroxide solution to give a solution of pH 7.5. To this stirred solution was added gradually an excess of a solution of potassium ferricyanide (0.01M, 11.4 ml), Hope et al., *J. Biol. Chem.*, vol. 237 (1962) at 1563. The yellow solution was stirred for 90 min more and for 1 h with anion-exchange resin (BioRad AG-3, Cl$^-$ form, 10 g damp weight). The suspension was filtered slowly through a bed of resin (80 g damp weight). The resin bed was washed with 300 ml of aqueous acetic acid and the combined filtrate and washings were lyophilized. The resulting powder (1386 mg) was desalted on a Sephadex G-15 column (110×2.7 cm) and eluted with aqueous acetic acid (50%) at a flow rate of 4 ml/h by the technique of Manning et al., *J. Chromatog.*, vol. 38 (1968) at 396. The eluate was fractionated and monitored for absorbance at 280 nm. The fractions comprising the major peak were pooled and lyophilized. The residue (55.5 mg) was further subjected to gel filtration on a Sephadex G-15 column (100×1.5 cm) and eluted with aqueous acetic acid (0.2M) at a flow rate of 2.5 ml/h. The peptide was eluted in a single peak (absorbance 280 nm). Lyophilization of the pertinent fractions yielded the vasopressin analog (49 mg, 37.3%); $R_f$(E) 0.19; $R_f$(F) 0.30; $[\alpha]_D^{22} = -59.6°$ (c 0.19, 1M, AcOH).

Amino acid analysis: Tyr 0.81; Phe, 1.01; Glu, 1.04; Asp, 0.98; Pro, 1.04; Arg, 0.95; Gly, 1.00; NH$_3$ 3.10. Analysis following performic acid oxidation prior to hydrolysis according to Moore, *J. Biol. Chem.*, vol. 238 (1963) at 235, gave a Cys(O$_3$H)—Gly ratio of 1.03:1.00.

(b) From Acyloctapeptide

Treatment of the acyloctapeptide (160 mg, 0.107 mmol) as described in Example 3(a) yielded the analog (64 mg, 51.7%), which was indistinguishable from the foregoing preparation by TLC: $[\alpha]_D^{23} = -59.1°$ (c 0.5, 1M AcOH).

Amino acid analysis: Tyr, 0.80; Phe, 1.02; Glu, 1.02; Asp, 0.98; Pro, 1.03; Arg, 0.96; Gly, 1.00; NH$_3$, 3.05. Analysis following performic acid oxidation prior to hydrolysis gave a Cys—(O$_3$H)—Gly ratio of 1.02:1.00.

EXAMPLE 4

[1-(β-Mercapto-β,β-cyclopentamethylenepropionic acid), 2-D-(O-methyltyrosine)]-arginine vasopressin The compound was made in the same manner as the compound of Example 3, except that D-O-methyltyrosine was used instead of O-methyltyrosine. The purity of the compound was determined by TLC with the following results:

$R_f$(E'): 0.08

$R_f$(F): 0.30

This compound is representative of arginine vasopressins, having a D-amino acid in the 2-position. The solvent designated E' is BAW 4:1:1 by volume.

EXAMPLE 5

[1-(β-Mercapto-β,β-cyclopentamethylenepropionic acid), 2-D-phenylalanine, 4-substituted]arginine vasopressins Compounds of this series were prepared as in Examples 1–4, obtaining protected intermediates for each analog. Coupling with β-(S-benzylmercapto)-β,β-cyclopentamethylenepropionate was done in accordance with Nestor, supra.

Each precursor was deblocked with sodium in liquid ammonia to produce a sulfhydryl compound. The latter compounds were oxidatively cyclized with potassium ferricyanide, as in the preceding Examples. The analogs were desalted and purified by gel filtration on Sephadex G-15 by a two-step procedure using 50% acetic acid and 0.2M acetic acid, respectively, as eluants. The purity and identity of each analog was ascertained by thin-layer chromatography in two different solvent systems, BAW (butan-1-ol-acetic acid, water 4:1:1 v/v) and BAWP (butan-1-ol-acetic acid-water-pyridine 15:3:3:10 v/v), with the following results:

| 4-substituent | $R_f$(BAW) | $R_f$(BAWP) |
|---|---|---|
| Val | 0.32 | 0.56 |
| Ile | 0.33 | 0.58 |
| Thr | 0.22 | 0.48 |
| Gln | 0.13 | 0.40 |
| Ala | 0.21 | 0.50 |
| Lys | 0.02 | 0.19 |
| Cha | 0.36 | 0.62 |
| Nva | 0.32 | 0.57 |
| Leu | 0.34 | 0.59 |
| Phe | 0.33 | 0.55 |
| Tyr | 0.31 | 0.53 |
| Gly | 0.19 | 0.47 |
| Abu | 0.28 | 0.53 |
| Nle | 0.34 | 0.59 |

EXAMPLE 6

[1-(β-Mercapto-β,β-cyclopentamethylenepropionic acid), 2-D-isoleucine, 4-substituted]arginine vasopressins Exemplary compounds of this series were made as in Example 5 and assayed using the same solvent systems for thin-layer chromatography.

Results were:

| 4-substituent | $R_f$(BAW) | $R_f$(BAWP) |
|---|---|---|
| Val | 0.28 | 0.49 |
| Abu | 0.25 | 0.47 |
| Ile | 0.29 | 0.51 |
| Thr | 0.20 | 0.44 |
| Ala | 0.36 | 0.44 |

EXAMPLE 7

Substituted vasopressins

Other vasopressin derivatives were made and characterized as in Examples 1–6. The following compounds were prepared:

| Compound | $R_f$(BAW) | $R_f$(BAWP) |
|---|---|---|
| d(CH$_2$)$_5$D-Phe$^2$Ile$^4$Phe(NH$_2$)$^8$VP | 0.19 | 0.80 |
| d(CH$_2$)$_5$D-Phe$^2$Ile$^4$Hy-Pro$^7$AVP | 0.10 | 0.39 |
| d(CH$_2$)$_5$D-Tyr(Et)$^2$Pro$^7$VAVP | 0.32 | 0.49 |
| d(CH$_2$)$_5$D-Tyr(Et)$^2$-Δ$^3$-Pro$^7$VAVP | 0.13 | 0.42 |
| d(CH$_2$)$_5$D-Tyr(Et)$^2$D-Pro$^7$VAVP | 0.12 | 0.63 |
| d(CH$_2$)$_5$Tyr(Et)$^2$D-Pro$^7$VAVP | 0.12 | 0.53 |
| d(CH$_2$)$_4$D-Tyr(Et)$^2$VAVP | 0.33 | 0.55 |
| d(CH$_2$)$_4$D-Tyr(Et)$^2$VDAVP | 0.15 | 0.77 |

EXAMPLE 8

Antagonism to the vasopressor response was estimated in accordance with Dyckes et al., *J. Med. Chem.*, vol. 17 (1974) at 969. The values are expressed as pA$_2$ values, defined as in Schild et al., *Br. J. Pharmacol.*, vol. 2 (1947) at 189.

Activity as antidiuretic agonists was determined by intravenous injection of the compounds being evaluated in ethanol-anesthesized water-loaded rats in accordance with Sawyer, *Endocrinology*, vol. 63 (1958) at 694. Antagonism of the response to subsequent injections of vasopressin was tested as described by Sawyer et al., *Science*, vol. 212 (1981) at 49.

Antagonistic potencies were determined and expressed as "effective doses" and pA$_2$ values. The "effective dose" is defined as the dose (in nanomoles per kilogram) that reduces the response seen from 2x units of agonist injected 20 min after the dose of antagonist to the response with 1x units of agonist. Estimated in vivo "pA$_2$" values represent the negative logarithms of the effective doses, divided by the estimated volume of distribution (67 ml/kg). Results are given in Tables 1 and 2.

The preceding examples can be repeated with similar success by substituting the generically or specifically described reactants and/or operating conditions of this invention for those used in the preceding Examples.

TABLE 1

| | Anti-Antidiuretic | | Antivasopressor | |
|---|---|---|---|---|
| Compound | ED nmoles/Kg | pA$_2$ | ED nmoles/Kg | pA$_2$ |
| d(CH$_2$)$_5$—D-TyrVAVP | 2.2 ± 0.2 | 7.51 ± 0.08 ± (4) | 0.29 ± 0.09 | 0.41 ± 0.11 (4) |
| d(CH$_2$)$_5$Tyr(Me)VDAVP | 15 ± 3 | 6.68 ± 0.11 (4) | 0.28 ± 0.05 | 8.44 ± 0.07 (8) |
| d(CH$_2$)$_5$Tyr(Et)VDAVP | 5.7 ± 0.5 | 7.10 ± 0.08 (4) | 0.34 ± 0.04 | 8.31 ± 0.05 (8) |
| d(CH$_2$)$_5$—D-Tyr(Me)VAVP | 1.2 ± 0.3 | 7.77 ± 0.07 (6) | 0.23 ± 0.04 | 8.48 ± 0.08 (4) |
| d(CH$_2$)$_5$—D-Tyr(Et)VAVP | 1.1 ± 0.2 | 7.81 ± 0.07 (5) | 0.45 ± 0.11 | 8.22 ± 0.12 (4) |
| d(CH$_2$)$_5$Tyr(Me)AVP | — | | 0.16 ± 0.01 | 8.62 ± 0.03 |
| d(CH$_2$)$_5$[D-Tyr(Me)$^2$]AVP | 7.3 ± 1.3 | 6.98 ± 0.08 (4) | 0.36 ± 0.02 | 8.27 ± 0.02 (5) |
| d(CH$_2$)$_5$Tyr(Me)$^2$D-Cys$^6$AVP | ~194 | 5.5 | 0.96 ± 0.24 | 7.87 ± 0.09 (4) |
| d(CH$_2$)$_5$D-Tyr(Et)$^2$Pro$^7$VAVP | 1.1 ± 0.2 | 7.81 ± 0.07 | 0.45 ± 0.11 | 8.22 ± 0.12 |
| d(CH$_2$)$_5$D-Tyr(Et)$^2$—Δ$^3$-Pro$^7$VAVP | 1.5 ± 0.2 | 7.66 ± 0.08 | 0.62 ± 0.04 | 8.03 ± 0.03 |
| d(CH$_2$)$_5$D-Tyr(Et)$^2$D-Pro$^7$VAVP | 1.6 ± 0.03 | 7.64 ± 0.08 | 0.55 ± 0.09 | 8.10 ± 0.06 |
| d(CH$_2$)$_5$Tyr(Et)$^2$D-Pro$^7$VAVP | 34.5 ± 7 | 6.32 ± 0.11 | 0.45 ± 0.15 | 8.23 ± 0.13 |
| d(CH$_2$)$_4$D-Tyr(Et)$^2$VAVP | 0.72 ± 0.17 | 8.04 ± 0.11 (6) | 0.50 ± 0.07 | 8.14 ± 0.07 (4) |
| d(CH$_2$)$_4$D-Tyr(Et)$^2$VDAVP | 0.97 ± 0.19 | 7.89 ± 0.11 (5) | 0.79 ± 0.08 | 7.93 ± 0.05 (4) |

TABLE 2

| | Anti-Antidiuretic | | Antivasopressor Potency | | |
|---|---|---|---|---|---|
| Compound | ED nmoles/Kg | pA$_2$ | ED nmoles/Kg | AD/VP | |
| d(CH$_2$)$_5$D-Phe$^2$VAVP | 0.67 ± 0.13 | 8.06 | 0.58 ± 0.04 | 0.9 | |
| d(CH$_2$)$_5$D-Phe$^2$Ile$^4$AVP | 0.46 ± 0.07 | 8.24 | 0.99 ± 0.12 | 2.2 | |
| d(CH$_2$)$_5$D-Phe$^2$Thr$^4$AVP | 1.7 ± 0.4 | 7.62 | 2.9 ± 0.5 | 1.7 | |
| d(CH$_2$)$_5$D-Phe$^2$AVP | 4.3 ± 0.6 | 7.21 | 0.30 ± 0.03 | 0.07 | |
| d(CH$_2$)$_5$D-Phe$^2$Ala$^4$AVP | 2.2 ± 0.7 | 7.52 | 1.9 ± 0.2 | 0.9 | |
| d(CH$_2$)$_5$D-Phe$^2$Lys$^4$AVP | 4.5 ± 1.9 | 7.22 | 7.9 ± 2.6 | 1.7 | |
| d(CH$_2$)$_5$D-Phe$^2$Cha$^4$AVP | 4.6 ± 0.9 | 7.19 | 9 ± 4 | 2.0 | |
| d(CH$_2$)$_5$D-Phe$^2$Nva$^4$AVP | 6.9 ± 0.09 | 6.99 | 1.4 ± 0.4 | 0.2 | |
| d(CH$_2$)$_5$D-Phe$^2$Leu$^4$AVP | 66 ± 19 | 6.07 | 1.3 ± 0.1 | 0.02 | |
| d(CH$_2$)$_5$D-Phe$^2$Phe$^4$AVP | 65 ± 15 | 6.07 | 25 ± 4 | 0.5 | |
| d(CH$_2$)$_5$D-Phe$^2$Tyr$^4$AVP | ~178 | ~5.57 | 22 ± 6 | 0.12 | |
| d(CH$_2$)$_5$D-Phe$^2$Gly$^4$AVP | 97 ± 10 | 5.85 | 11 ± 2 | 0.11 | |
| d(CH$_2$)$_5$D-Ile$^2$VAVP | 0.70 ± 0.08 | 7.98 | 8.2 ± 1.4 | 12 | |
| d(CH$_2$)$_5$D-Ile$^2$Abu$^4$AVP | 0.41 ± 0.05 | 8.22 | 12 ± 1.3 | 29 | |
| d(CH$_2$)$_5$D-Ile$^2$Ile$^4$AVP | 0.67 ± 0.15 | 8.04 | 26 ± 3 | 39 | |
| d(CH$_2$)$_5$D-Ile$^2$Thr$^4$AVP | 0.88 ± 0.18 | 7.91 | 10.5 ± 1.2 | 12 | |
| d(CH$_2$)$_5$D-Ile$^2$Ala$^4$AVP | 1.70 ± 0.5 | 7.76 | 66 ± 5 | 39 | |
| d(CH$_2$)$_5$D-Ile$^2$AVP | 8.3 ± 2.7 | 6.96 | 1.25 ± 0.3 | 0.04 | |
| d(CH$_2$)$_5$D-Phe$^2$Abu$^4$AVP | 0.77 ± 0.12 | 7.96 | 1.4 ± 0.3 | 1.8 | |
| d(CH$_2$)$_5$D-Phe$^2$Nle$^4$AVP | 5.6 ± 1.3 | 7.12 | 2.1 ± 0.3 | 0.4 | |
| d(CH$_2$)$_5$D-Ile$^2$Leu$^4$AVP | 11 ± 2 | 6.80 | 12.2 | 1.1 | |
| d(CH$_2$)$_5$D-Phe$^2$Ile$^4$Phe(NH$_2$)$^8$VP | >398 | <5.2 | 31 ± 6 | <0.1 | |
| d(CH$_2$)$_5$D-Phe$^2$Ile$^4$Hy-Pro$^7$AVP | 1.3 ± 0.3 | 7.74 | 0.9 ± 0.2 | 0.7 | |
| d(CH$_2$)$_5$Tyr(Et)$^2$Val$^4$Lys$^8$VP | 3.9 ± 0.7 | 7.29 | 0.67 ± 0.09 · | 0.2 | |
| d(CH$_2$)$_5$D-Tyr(Et)$^2$Val$^4$Lys$^8$VP | 1.5 ± 0.4 | 7.72 | 0.48 ± 0.08 | 0.3 | |
| d(CH$_2$)$_5$D-Ile$^2$Val$^4$Orn$^8$VP | 1.5 ± 0.2 | 7.66 | 16 + 2 | 11 | |

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula

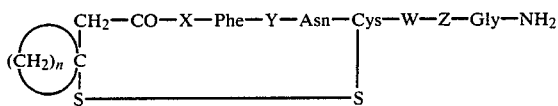

wherein n is 4 or 5; X is D—Tyr(R), D—Phe, D—Val, D—Leu, D—Ile, D—Nva, D—Nle, D—Cha, D—Abu, D—Thr, D—Met, D—Asn or D—Gln; Y is Ile, Thr, Gln, Ala, Lys, Cha, Nva, Nle, Orn, Ser, Asn, Abu, Met or Leu; W is (D— or L—)Pro, Hy—Pro or $\Delta^3$—Pro; Z is (D— or L—)Arg, Orn or Hys and R is methyl, ethyl, propyl or butyl.

2. A compound of claim 1, having the formula

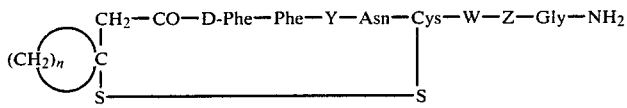

wherein n is 4 or 5; Y is Ile, Thr, Gln, Ala, Lys, Cha, Nva, Orn, Ser, Asn, Abu, Nle or Leu; W is (D— or L—)Pro, $\Delta^3$—Pro or Hy—Pro and Z is (D— or L—)Arg, Orn or Lys.

3. A compound of claim 2, wherein n is 5, W is Pro and Z is (D— or L—)Arg.

4. A compound of claim 2, wherein Y is Ile, Thr, Ala or Abu.

5. [1-($\beta$-Mercapto-$\beta$,$\beta$-cyclopentamethylenepropionic acid), 2-D-phenylalanine, 4-isoleucine]-arginine vasopressin, a compound of claim 2.

6. [1-($\beta$-Mercapto-$\beta$,$\beta$-cyclopentamethylenepropionic acid), 2-D-phenylalanine, 4-threonine]-arginine vasopressin, a compound of claim 2.

7. [1-($\beta$-Mercapto-$\beta$,$\beta$-cyclopentamethylenepropionic acid), 2-D-phenylalanine, 4-alanine]-arginine vasopressin, a compound of claim 2.

8. [1-($\beta$-Mercapto-$\beta$,$\beta$-cyclopentamethylenepropionic acid), 2-D-phenylalanine, 4-$\alpha$-aminoisobutyric acid]-arginine vasopressin, a compound of claim 2.

9. A compound of claim 1, having the formula

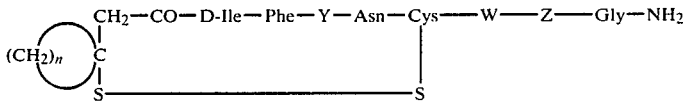

wherein n is 4 or 5; Y is Gln, Ala, Lys, Cha, Nva, Orn, Leu, Ser, Asn, Met, Nle, Abu, Ile or Thr; W is (D— or L—)Pro, Hy—Pro or $\Delta^3$—Pro and Z is (D— or L—)Arg, Lys or Orn.

10. A compound of claim 9, wherein n is 5, W is Pro and Z is (D— or L—)Arg.

11. A compound of claim 9, wherein Y is Abu, Ala, Ile or Thr.

12. [1-($\beta$-Mercapto-$\beta$,$\beta$-cyclopentamethylenepropionic acid), 2-D-isoleucine, 4-$\alpha$-aminobutyric acid]-arginine vasopressin, a compound of claim 9.

13. [1-($\beta$-Mercapto-$\beta$,$\beta$-cyclopentamethylenepropionic acid), 2-D-isoleucine, 4-isoleucine]-arginine vasopressin, a compound of claim 9.

14. [1-($\beta$-Mercapto-$\beta$,$\beta$-cyclopentamethylenepropionic acid), 2-D-isoleucine, 4-threonine[-arginine vasopressin, a compound of claim 9.

15. [1-($\beta$-Mercapto-$\beta$,$\beta$-cyclopentamethylenepropionic acid), 2-D-isoleucine, 4-alanine]-arginine vasopressin, a compound of claim 9.

16. A compound of claim 1, having the formula

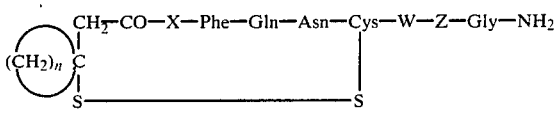

wherein n is 4 or 5; X is D—Tyr(R); R is methyl, ethyl, propyl or butyl; W is (D— or L—)Pro, Hy—Pro or $\Delta^3$—Pro and Z is (D— or L—)Arg, Lys or Orn.

17. A compound of claim 16, wherein n is 5, W is Pro and Z is (D— or L—)Arg.

18. A compound of claim 16, wherein X is D—Tyr(Me).

19. A method for antagonizing the in vivo response of an animal to the antidiuretic action of an antidiuretic hormone, comprising administering to the animal being treated an amount of a compound of claim 1, in admixture with a physiologically and pharmaceutically acceptable carrier, effective to antagonize the antidiuretic response to the antidiuretic hormone.

20. The method of claim 19, wherein the antidiuretic hormone is arginine vasopressin.

21. The method of claim 19, wherein the compound is administered parenterally.

22. A method for antagonizing the in vivo response of an animal to the antidiuretic action of an antidiuretic hormone, comprising administering to the animal being treated a compound of claim 2, in admixture with a physiologically and pharmaceutically acceptable carrier, effective to antagonize the antidiuretic response to the antidiuretic hormone.

23. A method for antagonizing the in vivo response of an animal to the antidiuretic action of an antidiuretic hormone, comprising administering to the animal being treated an amount of a compound of claim 5, in admixture with a physiologically and pharmaceutically acceptable carrier, effective to antagonize the antidiuretic response to the antidiuretic hormone.

24. A method for antagonizing the in vivo response of an animal to the antidiuretic action of an antidiuretic hormone, comprising administering to the animal being treated an amount of a compound of claim 9, in admixture with a physiologically and pharmaceutically acceptable carrier, effective to antagonize the antidiuretic response to the antidiuretic hormone.

25. A method for antagonizing the in vivo response of an animal to the antidiuretic action of an antidiuretic hormone, comprising administering to the animal being treated an amount of a compound of claim 11, in admixture with a physiologically and pharmaceutically acceptable carrier, effective to antagonize the antidiuretic response to the antidiuretic hormone.

26. A method for antagonizing the in vivo response of an animal to the antidiuretic action of an antidiuretic hormone, comprising administering to the animal being treated an amount of a compound of claim 16, in admixture with a physiologically and pharmaceutically acceptable carrier, effective to antagonize the antidiuretic response to the antidiuretic hormone.

* * * * *